(12) United States Patent
Cohen et al.

(10) Patent No.: US 6,797,519 B2
(45) Date of Patent: Sep. 28, 2004

(54) METHOD AND APPARATUS FOR DIAGNOSING HEMOSTASIS

(75) Inventors: Eli Cohen, Skokie, IL (US); Irene A. Navickas, Northbrook, IL (US); Benjamin M. Cohen, Skokie, IL (US); Barry N. Robinson, Chicago, IL (US)

(73) Assignee: Haemoscope Corporation, Niles, IL (US)

( * ) Notice: Subject to any disclaimer, the term of this patent is extended or adjusted under 35 U.S.C. 154(b) by 284 days.

(21) Appl. No.: 09/974,044

(22) Filed: Oct. 10, 2001

(65) Prior Publication Data

US 2003/0073244 A1 Apr. 17, 2003

(51) Int. Cl.[7] ............................................. G01N 33/86
(52) U.S. Cl. ...................... 436/69; 422/73; 600/369; 705/2; 709/217
(58) Field of Search ...................... 436/63, 69; 435/13; 422/73; 73/64.41; 600/369; 705/2.3; 700/266; 709/217

(56) References Cited

U.S. PATENT DOCUMENTS

| | | | |
|---|---|---|---|
| 4,695,956 A | | 9/1987 | LeVeen et al. |
| 5,023,785 A | | 6/1991 | Adrion et al. ......... 364/413.08 |
| 5,167,145 A | | 12/1992 | Butler et al. |
| 6,060,323 A | | 5/2000 | Jina |
| 6,225,126 B1 | * | 5/2001 | Cohen et al. .................. 436/69 |
| 6,537,819 B2 | * | 3/2003 | Cohen et al. .................. 436/69 |
| 6,613,573 B1 | * | 9/2003 | Cohen .......................... 436/69 |
| 2002/0107452 A1 | * | 8/2002 | Kwong ....................... 600/509 |
| 2002/0173991 A1 | * | 11/2002 | Avitall ............................ 705/2 |
| 2002/0178126 A1 | * | 11/2002 | Beck et al. ..................... 705/75 |
| 2002/0198740 A1 | * | 12/2002 | Roman et al. ................. 705/3 |

FOREIGN PATENT DOCUMENTS

WO   01/50950   * 7/2001

OTHER PUBLICATIONS

Nguyen et al. Arch. Pathol. Lab. Med., vol. 124, Apr. 2000, pp. 588–593.*

Steve Von Kier et al., *Hemostatic Product Transfusions and Adverse Outcomes: Focus on Point–of–Care Testing to Reduce Transfusion Need*, Journal of Cardiothoracic and Vascular Anesthesia, 2000, pp. 15–21, vol. 14, No. 3, Suppl. 1.

S. V. Mallett et al., *Thrombelastography*, British Journal of Anaesthesia, 1992, pp. 307–313, vol. 69, No. 3.

Kenneth J. Tuman et al., *Effects of Progressive Blood Loss on Coagulation as Measured by Thrombelastography*, Anesth Analg, 1987, pp. 856–863, vol. 66.

Shiv K. Sharma et al., *Management of a Postpartum Coagulopathy Using Thrombelastography*, Journal of Clinical Anesthesia, 1997, pp. 243–247, vol. 9.

(List continued on next page.)

*Primary Examiner*—Maureen M. Wallenhorst
(74) *Attorney, Agent, or Firm*—Marshall, Gerstein & Borun LLP (57) ABSTRACT

A system and method for diagnosing hemostasis utilizing a communication network. A blood hemostasis analyzer tests a blood sample and provides a parameter indicative of hemostasis. The blood hemostasis analyzer is communicatively coupled via the communication network to an analysis tool. The analysis tool includes an algorithm operable on the parameter to provide a result. The diagnostic result may indicate normal hemostasis, a coagulopathy or other condition, and may provide a recommended course of treatment.

20 Claims, 6 Drawing Sheets

OTHER PUBLICATIONS

YooGoo Kang, M.D. et al., *Epsilon–aminocaproic Acid for Treatment of Fibrinolysis During Liver Transplantation*, Anesthesiology, 1987, pp. 766–773, vol. 66, No. 6.

YooGoo Kang et al., *Blood Coagulation During Liver, Kidney, Pancreas, and Lung Transplantation*, Perioperative Transfusion Medicine, 1998, pp. 471–492.

Shiv K. Sharma, M.D. et al., *Assessment of Changes in Coagulation in Parturients with Preeclampsia Using Thromboelastography*, Anesthesiology, 1999, pp. 385–390, vol. 90, No. 2.

S. Vig et al., *Thromboelastography: A Simple Screen for Hypercoagulable States, Hyperhomocysteinaemia and a Predictor of Failure Following Peripheral Arterial Invervention*, 1999.

Bruce D. Spiess, *Perioperative Coagulation Monitoring*, Perioperative Transfusion Medicine, 1998, pp. 239–257.

T. G. Ruttmann et al., *Haemodilution Induces a Hypercoagulable State*, British Journal of Anaesthesia, 1996, pp. 412–414, vol. 76.

K. F. G. NG et al., *The Development of Hypercoagulability State, as Measured by Thrombelastography, Associated with Intraoperative Surgical Blood Loss*, Anaesthesia and Intensive Care, 1996, pp. 20–25, vol. 24, No. 1.

N. M. Gibbs et al., *Thrombelastographic Patterns Following Abdominal Aortic Surgery*, Anaesthesia and Intensive Care, 1994, pp. 534–538, vol. 22, No. 5.

Bruce D. Spiess et al., *Thromboelastography: A Coagulation–monitoring Technique Applied to Cardiopulmonary Bypass*, pp. 163–181, 1988.

Yoo Goo Kang, M.D. et al., *Intraoperative Changes in Blood Coagulation and Thrombelastographic Monitoring in Liver Transplantation*, Anesth Analg, 1985, pp. 888–896, vol. 64.

Brian P. Heather et al., *The Saline Dilution Test—A Preoperative Predictor of DVT*, Br. J. Surg., 1980, pp. 63–65, vol. 67.

YooGoo Kang, M.D., *Thromboelastography in Liver Transplantation*, Seminars in Thrombosis and Hemostasis, 1995, pp. 34–44, vol. 21, Suppl. 4.

Joseph A. Caprini et al., *The Identification of Accelerated Coagulability*, Thrombosis Research, 1976, pp. 167–180, vol. 9, No. 2.

H. W. Grant et al., *Prediction of Neonatal Sepsis by Thromboelastography*, Pediatr. Surg. Int., 1997, pp. 289–292, vol. 12.

R. K. S. Whitta et al., *Thrombelastography Reveals Two Causes of Haemorrhage in HELLP Syndrome*, British Journal of Anaesthesia, 1995, pp. 464–468, vol. 74.

S. N. Mardel et al., *Reduced Quality of Clot Formation with Gelatin–based Plasma Substitutes*, British Journal of Anaesthesia, 1998, pp. 204–207, vol. 80.

Yoo Goo Kang, M.D., *Monitoring and Treatment of Coagulation*, pp. 151–173, date unknown.

R. Rai et al., *Prepregnancy Thrombophilic Abnormalities are Associated with Subsequent Miscarriage*.

K. F. J. Ng et al., *In Vivo Effect of Haemodilution with Saline on Coagulation: A Randomized Controlled Trial*, British Journal of Anaesthesia, 2002, pp. 475–480, vol. 88, No. 4.

Christoph R. Kaufmann, M.D. et al., Usefulness of *Thrombelastography in Assessment of Trauma Patient Coagulation*, The Journal of Trauma: Injury, Infection, and Critical Care, 1997, pp. 716–722, vol. 42, No. 4.

D. Royston et al., *Reduced Haemostatic Factor Transfusion Using Heparinase–modified Thrombelastography During Cardiopulmonary Bypass*, British Journal of Anaesthesia, 2001, pp. 575–578, vol. 86, No. 4.

Paul D. Mongan, M.D. et al., *The Role of Desmopressin Acetate in Patients Undergoing Coronary Artery Bypass Surgery*, Anesthesiology, 1992, pp. 38–46, vol. 77.

J. A. Caprini et al., *Postoperative Hypercoagulability and Deep–vein Thrombosis After Laparoscopic Cholecystectomy*, Surgical Endoscopy, 1995, pp. 304–309, vol. 9.

Linda Shore–Lesserson, M.D. et al., *Thromboelastography–guided Transfusion Algorithm Reduces Transfusions in Complex Cardiac–Surgery–Anesth–Analg*, 1999, pp. 312–319, vol. 88.

Frenette et al., "Effectiveness of Conjugated Estrogen in Orthotopic Liver Transplantation," Southern Medical Journal, vol. 91, No. 4, Apr. 1998, pp. 365–368.

International Search Report for Application No. PCT/US03/30710 dated Apr. 21, 2004.

* cited by examiner

Normal  *FIG. 7A*

Anticoagulants/hemophilia  *FIG. 7B*

Platelet inhibition/dysfunction  *FIG. 7C*

Primary fibrinolysis  *FIG. 7D*

Hypercoagulation  *FIG. 7E*

D.I.C. Stage 1  *FIG. 7F*

D.I.C. Stage 2  *FIG. 7G*

METHOD AND APPARATUS FOR DIAGNOSING HEMOSTASIS

FIELD OF THE INVENTION

The present invention relates generally to the field of hemostasis, and more particularly, the present invention relates to methods and apparatus for communicating measured characteristics of a blood sample via an electronic network for the purpose of diagnosing hemostasis.

BACKGROUND OF THE INVENTION

The Clinical Hemostasis Handbook, by Laposata et al., defines normal hemostasis as the "controlled activation of clot formation and clot lysis that stops hemorrhage without permitting inappropriate thrombosis." This means that hemostasis is the net result of two systems working in tandem, the coagulation system—the system that produces the clot, and the fibrinolytic system—the system that dissolves the clot. When the balance between the two systems shifts towards procoagulation, the result is thrombosis. When the balance shifts toward fibrinolysis, the result is hemorrhage. Therefore, a hemostasis test that does not measure the net product of both the coagulation and fibrinolytic systems, such as provided by the TEG® haemostasis analyzer available from Haemoscope Corporation of Niles, Ill., will fail to properly analyze patient hemostasis. For example, in the case of fibrinolysis secondary to hypercoagulability, D-dimer, fibrinogen degradation product (FDP) and fibrinogen split product (FSP) tests would show high fibrinolytic activity, while prothrombin time (PT) and activated partial thromboplastin time (aPTT) results would be normal due to their inherent lack of sensitivity to the hypercoagulable state. Based on these results, antifibrinolytic drugs might be prescribed, shutting off the fibrinolytic system, producing an imbalance toward procoagulability, and could result in acute myocardial infarct, stroke, etc.

Recent advances in the understanding of hemostasis mechanisms have recognized the value of whole-blood monitoring techniques such as provided by the TEG® haemostasis analyzer. As a result, the older view of a separate intrinsic and extrinsic coagulation system has been abandoned along with the waterfall descriptions of coagulation mechanisms with one enzyme working after another and with some mechanisms of feedback amplification and inhibition derived in a plasma milieu. None of this theory was actually applicable in moving blood. These concepts have been replaced by a concept of enzyme complexes existing on the surface of cells, passing one another their substances until the final product, fibrin, is formed. The cell surfaces of importance are those of the platelets, which are activated and adhere to the site of injury. They localize the clotting process, enhance their activities, protect the enzyme complexes from inhibitors that circulate, and protect against propagation of the clotting activation downstream.

The surface concept provides an explanation of how some individuals with only a few percent of plasma coagulation factors can maintain hemostasis, while these same individuals will hemorrhage if their platelet function is compromised. Since prior tests were designed to use substitutes for platelet surfaces, it is readily understood why these tests do not agree with the whole-blood analysis technique, which uses the actual cellular surfaces to monitor hemostasis. Once the importance of the platelet surfaces and of other cellular surfaces and their interactions with the hemostasis process is understood, the value of prior tests comes into question.

Since the whole-blood analysis techniques, such as provided by the TEG® haemostasis analyzer, is sensitive to platelet function, plasma factors, activators, and inhibitors of coagulation, it represents an ideal monitor for hemostasis.

The whole-blood analysis technique used by the TEG® haemostasis analyzer allows acquisition of continuous quantitative information on the developing clot; the time it takes for the first fibrin to develop, the kinetics of clot development and the strength and stability of the clot, taking into consideration all of the components that make blood clot or lyse. Ignoring the interactive nature of hemostasis by analyzing separated blood components such as plasma, red blood cells, white blood cells, platelets, fibrinogen level or factor assay can result in artifacts that do not reflect the clinical condition. This should serve as a caution against basing therapy on these analyses alone, especially since there are significant risks associated with blood transfusions. Also, measuring single factors quantitatively can be misleading because the quantity, as measured by an assay, does not reflect the actual functional activity. Functional activity of a factor also depends on the presence and activity of activators, inhibitors, and cellular elements.

The TEG® haemostasis analyzer is an effective point-of-care test of hemostasis that can identify whether a patient has normal hemostasis, and if not, whether the abnormality is due to surgical, coagulopathy, or residual anticoagulation therapy. If the patient has a coagulopathy, the test results provided by the TEG® haemostasis analyzer can be used to identify the specific therapy to treat the condition. For example, the results can be used to determine if the patient needs fresh frozen plasma, cryoprecipitate, platelets, antifibrinolytic drugs, or thrombolytic drugs. In fact, potential therapies can first be applied in vitro to confirm their effect on the patient's blood sample before the patient is treated, and the in vivo effect may be evaluated by subsequent testing of the patient. This has been demonstrated by Kang et al., who found that "[t]he judicious use of a small dose of ε-aminocaproic acid, when its efficacy was confirmed in vitro (using results provided by a TEG® haemostasis analyzer), effectively treated the severe fibrinolysis without clinical thrombotic complications. In a prospective study of cardiac surgery, Shore-Lesserson concluded "the use of [whole-blood] analysis (provided by a TEG® haemostasis analyzer) in a transfusion algorithm allowed for identification and appropriate treatment of specific interoperative abnormalities of hemostasis. This intervention resulted in fewer postoperative transfusions and improved hemostasis. [R]esults (provided by a TEG® haemostasis analyzer) are readily available in the operating room thus making it effective as a point-of-care coagulation monitor."

Thus, the TEG® haemostasis analyzer is a monitoring device, like the EKG, in that it is run to confirm that patient hemostasis is normal, and can assist the physician's differential diagnosis of coagulopathy and guide a selective treatment with blood components and suitable pharmacological therapy. The analysis provided by the TEG® haemostasis analyzer is not intended to replace standard laboratory tests, such as the various separate blood component tests. The TEG® haemostasis analyzer will provide the physician an indication of whether the patient has normal hemostasis. If yes, then the use of laboratory tests will add unnecessary cost and/or provide misleading information. However, when the TEG® haemostasis analyzer shows coagulopathy, the results in conjunction with other laboratory tests assist in differential diagnosis and treatment.

Recently, due to dramatic changes in health care systems worldwide, the reduction of cost has become a prominent factor in the economic survival of the healthcare system. Use of whole-blood monitoring techniques in connection with diagnosis of hemostasis, and particularly the TEG® haemostasis analyzer, can reduce or eliminate the number of laboratory tests ordered for a patient and can be instrumental in reducing blood component transfusions. However, because of the complexity of the process of hemostasis, it is important that the physician fully understand the indications associated with the whole-blood testing results. These issues, however, typically arise during surgery or other invasive procedures such as cardiac catheterization or angioplasty, in trauma situations such as gunshot or knife wounds in the emergency room (ER), in obstetrics, and in intensive care environments, where the physician's attention is being drawn to numerous other patient considerations, and a hematologist may not be available or may require guidance. Thus, there is a need for a method and apparatus for quickly and accurately analyzing hemostasis test results and for providing the treating physician with diagnosis and therapy options.

DETAILED DESCRIPTION OF THE PREFERRED EMBODIMENTS

In accordance with a preferred embodiment of the invention, a hemostasis analyzer is operable for testing a blood sample and producing a hemostasis parameter indicative of hemostasis and includes an interface for coupling the hemostasis analyzer to a communication network. Following testing of a blood sample, the hemostasis analyzer communicates the hemostasis parameter via the communication network to an analysis tool coupled to the communication network. The analysis tool includes an algorithm for analyzing the hemostasis parameter and generating a diagnostic result. The diagnostic result may include a coagulopathy therapy recommendation or an additional testing indication. The blood sample may be treated in vitro, and the result may be an indication of the potential efficacy of the proposed treatment. The actual efficacy of the treatment may be evaluated by in vivo testing.

In another embodiment of the invention, the hemostasis analyzer is communicatively coupled to a workstation, such as a personal computer, personal digital assistant, or similar device and the parameter is provided to the workstation, either by direct communication or by manual entry. The workstation is in communication with the analysis tool via the communication network. The workstation may further include a database for retaining patient information, such as demographic data, medical history, treatment history, etc., which may be communicated with the parameter to the analysis tool.

The hemostasis analyzer may provide multiple parameters indicative of hemostasis, and the algorithm of the analysis tool may consider one or more of the multiple parameters to provide the diagnostic result.

The parameter may be graphically depicted, and the algorithm may employ signature analysis techniques in connection with the graphic depiction to provide the result.

The hemostasis analyzer may calculate one or more parameters, including without limitation, clotting time, clot kinetics, clot strength and lysis time that are communicated to the analysis tool for providing the diagnostic result. Other parameters, both objective and subjective, may also be determined, communicated to the analysis tool and utilized to provide the diagnostic result.

At the outset it should be noted that the invention is described in terms of several preferred embodiments relating to hemostasis. It will be appreciated that the invention has applicability to other areas of medicine where patient related data is measured and/or observed and where diagnoses is made based upon such measured and/or observed data.

Figure 1:
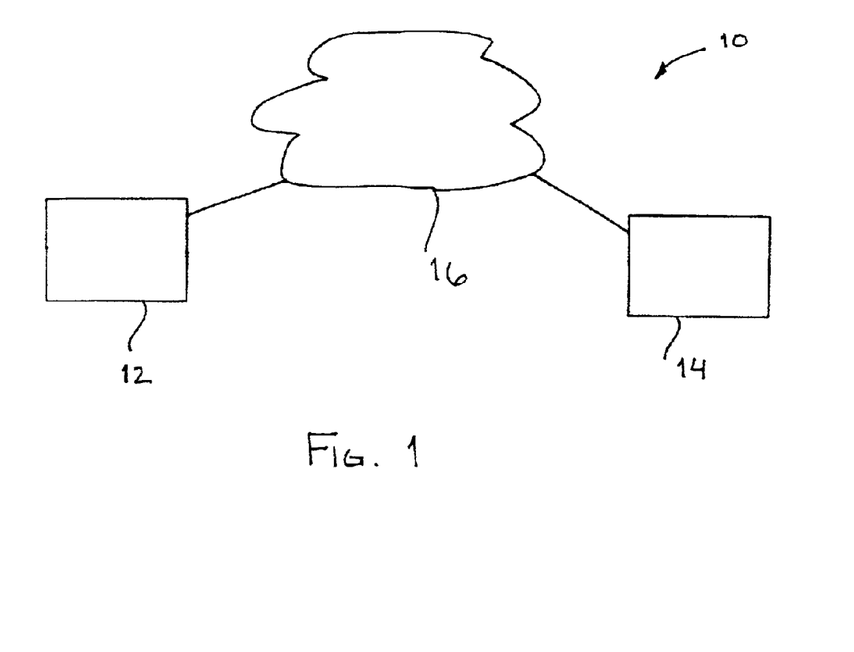
FIG. 1 is a block diagram of a system in accordance with a preferred embodiment of the invention.

A system 10 is shown in FIG. 1 that includes a hemostasis analyzer 12 and an analysis tool 14. The hemostasis analyzer may be a TEG® haemostasis analyzer available from Haemoscope Corporation of Niles, Ill., which is capable of producing multiple parameters indicative of hemostasis from a blood sample, although other devices and tests for providing parameters indicative of hemostasis may be used, such as separate blood component tests. Both the hemostasis analyzer 12 and the analysis tool 14 are communicatively coupled to a network 16, such as a hospital local area network (LAN) or hospital information system (HIS), a secure network, the Internet, and the like, for communicating information in accordance with an appropriate communication protocol, such as transfer control protocol/Internet protocol (TCP/IP). Where the network is the Internet, the hemostasis analyzer 12 and the analysis tool 14 may be coupled by a secure communication link, e.g., an IPsec or other suitable secure link. Where the network is a LAN or HIS, it may not be necessary to provide a secure communication link. The requirement for secure data communication will be established based upon the particular application.

Figure 2:
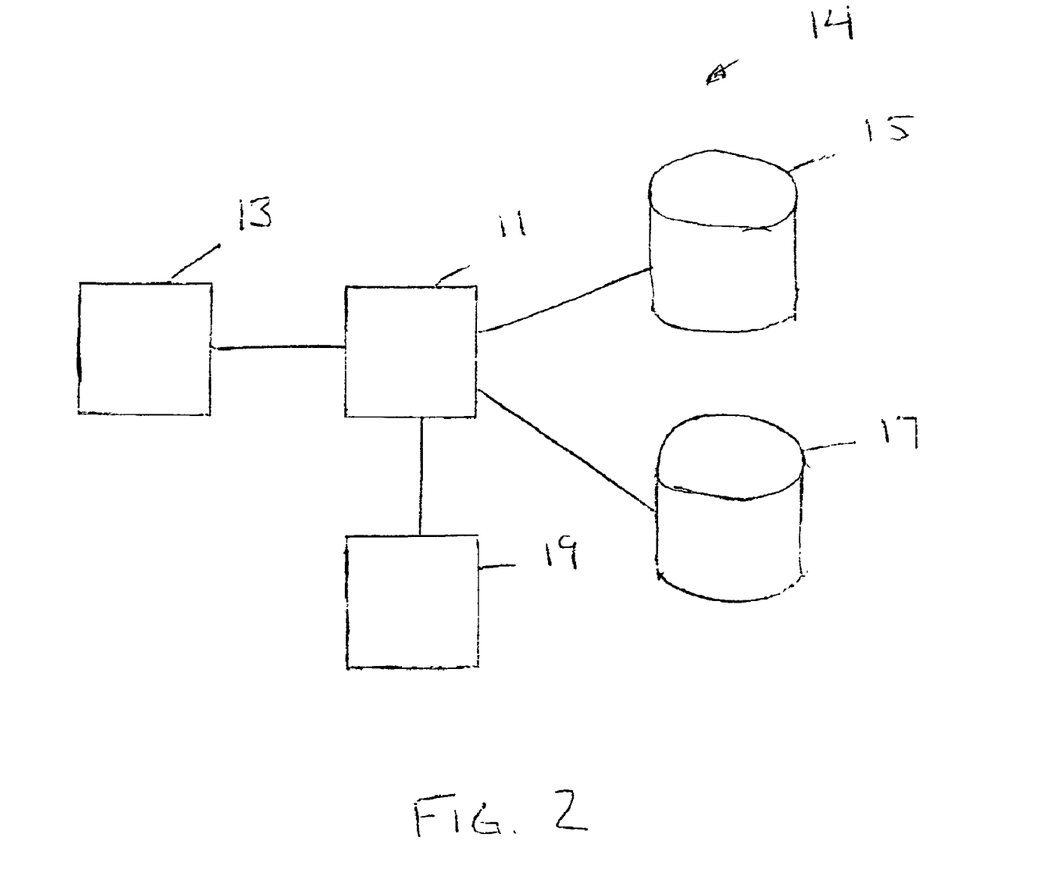
FIG. 2 is a block diagram of an analysis tool that may be used in the system illustrated in FIG. 1.

The analysis tool 14 may be a suitable computer platform, such as an Intel or compatible processor based computer utilizing the Windows operating environment, an Intel or compatible processor based computer utilizing the Linux operating environment, a PowerPC processor based computer utilizing the MAC OS operating environment, or any other suitable computer and operating system that may be communicatively coupled to the network 16. Referring to FIG. 2, the analysis tool 14 may include a processor 11, a user interface 13, a memory 19 retaining a control program for operating the processor, a database 15 containing model data and a database 17 containing patient related data. The databases 15 and 17 and the memory 19 are shown as separate elements for clarity of description, but it will be appreciated that these memory and storage elements may be implemented in a combined manner. Alternatively, the analysis tool 14 may be contained as an application retained on a personal digital assistant (PDA) such as a PALM OS based PDA, a Java, Wireless Application Protocol (WAP) or similarly enabled wireless communication device such as a cellular phone or pager, or other similar portable device. When used in connection with a portable device, the network may be a wireless communication network, e.g., a radio frequency based wireless network, an optical communication network, etc. Suitable radio frequency communication technologies, such as wireless packet data, Bluetooth, IEEE 802.11x, etc., and optical communication technologies, such as infrared, laser, etc. are well known to one of ordinary skill in the art.

Figure 3:
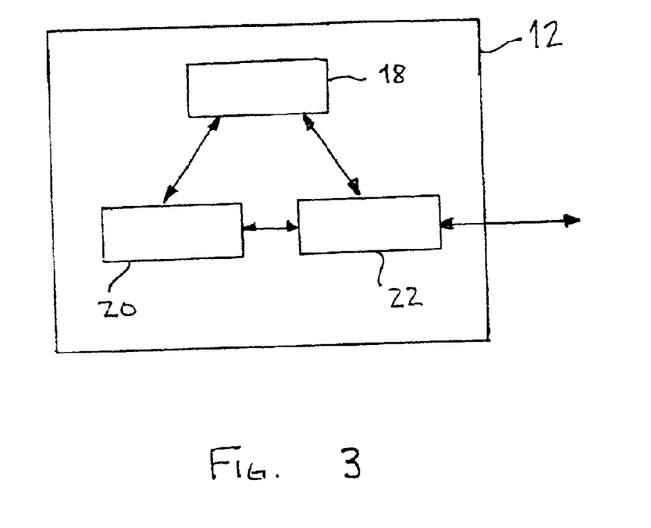
FIG. 3 is a block diagram of a hemostasis analyzer that may be used in the system illustrated in FIG. 1.

Referring to FIG. 3, the hemostasis analyzer 12 includes a testing portion 18, a user interface 20, and a communication interface 22. The user interface 20 may include mice, keyboards, barcode scanners, touch screens, push buttons, voice activation, indicator lights, alpha/numeric displays, a liquid crystal display (LCD), etc. that permit the user to operate the testing portion 18. Alternatively, the user interface 20 may include a computer coupled to the testing portion 18, the computer including a computer program stored in a memory thereof for interfacing with the testing portion 18 for initiating sample analysis and for collecting parameters from the testing portion 18. The communication interface 22 may be a network interface to the Internet or a LAN or HIS. Alternatively, the communication interface 22 may be a wireless interface. As noted above, the hemostasis analyzer 12 may be a TEG® haemostasis analyzer available from Haemoscope Corporation of Niles, Ill., which includes both analog outputs and digital outputs for coupling the device to a suitable computer platform.

Figure 6:
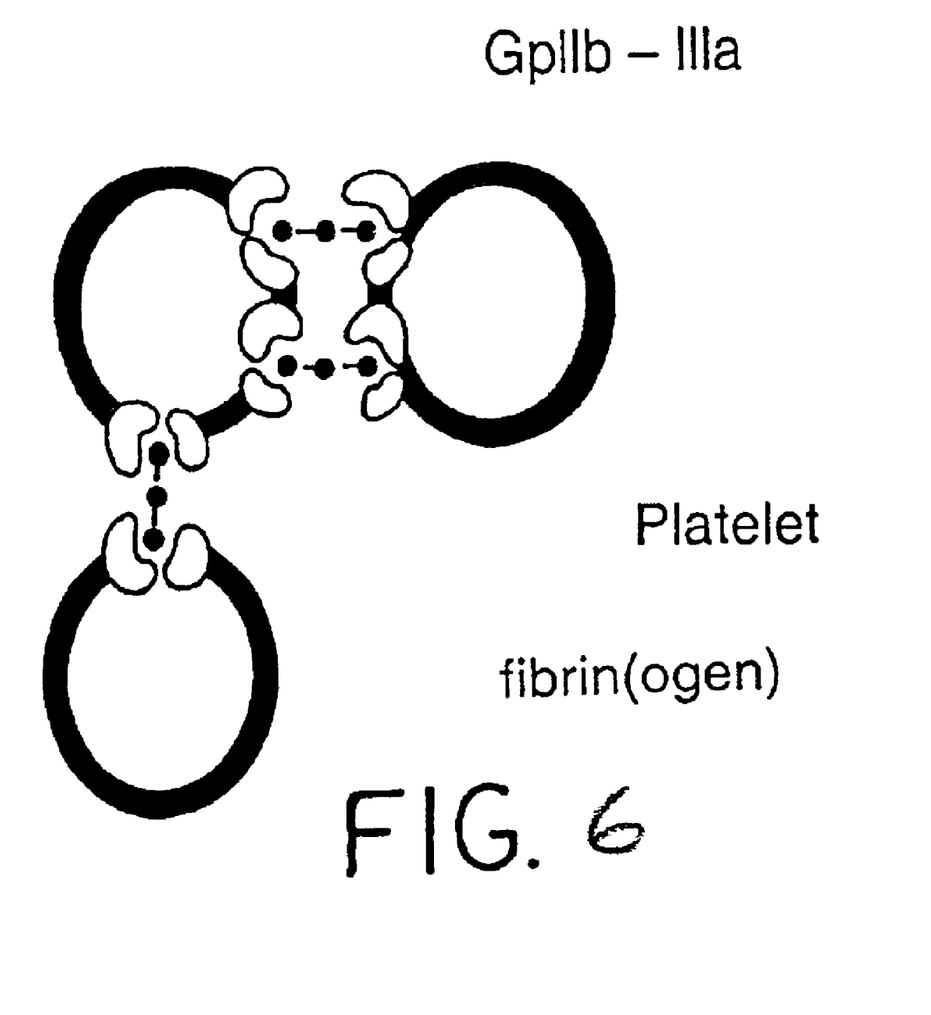
FIG. 6 is a graphic representation of the end result of the clot formation process.

The testing portion 18 includes the mechanical, electromechanical, control elements and software for effecting analysis of a blood sample to produce a parameter. To understand the operation of the hemostasis analyzer 12, however, it is useful first to understand the process of hemostasis. Hemostasis is a dynamic, extremely complex process involving many interacting factors, which include coagulation and fibrinolytic proteins, activators, inhibitors and cellular elements, such as platelet cytoskeleton, platelet cytoplasmic granules and platelet cell surfaces. The end result of the hemostasis process is a three-dimensional network of polymerized fibrin(ogen) fibers which together with platelet glycoprotein IIb/IIIa (GPIIb/IIIa) receptor bonding forms the final clot (see FIG. 6 illustrating graphically the final clot formation). A unique property of this network structure is that it behaves as a rigid elastic solid, capable of resisting deforming shear stress of the circulating blood. The strength of the final clot to resist deforming shear stress is determined by the structure and density of the fibrin fiber network and by the forces exerted by the participating platelets.

Figure 5:
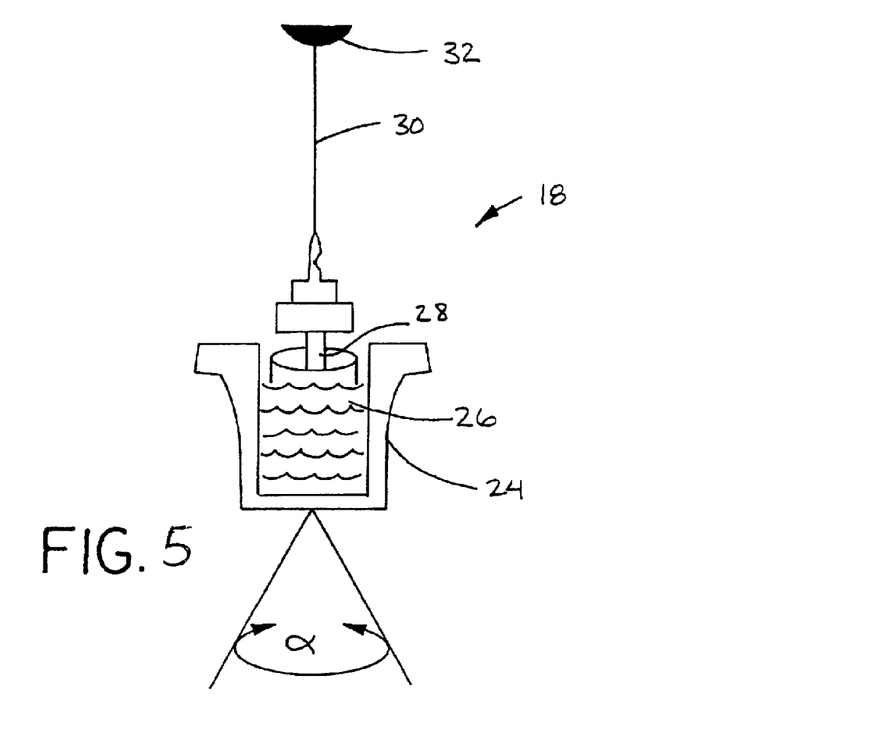
FIG. 5 is a schematic illustration of hemostasis analyzer.

An exemplary hemostasis analyzer 12 is described in detail in U.S. Pat. No. 6,225,126, issued May 1, 2001, entitled "Method and Apparatus for Measuring Hemostasis," and a complete discussion is not repeated here. With reference to FIG. 5, to assist in the understanding of the invention, however, a brief description of the blood hemostasis analyzer 12 is provided. The testing portion 18 uses a special cylindrical cup 24 that holds a blood sample 26. The cup 24 is coupled to a drive mechanism that causes the cup to oscillate through an angle α, preferably about 4°45'. Each rotation cycle lasts approximately 10 seconds. A pin 28 is suspended in the blood sample 26 by a torsion wire 30, and the pin 28 is monitored for motion. The torque of the rotating cup 24 is transmitted to the immersed pin 28 only after fibrin and/or fibrin-platelet bonding has linked the cup 24 and pin 28 together. The strength of these fibrin and/or fibrin-platelet bonds affects the magnitude of the pin motion, such that strong clots move the pin 28 directly in phase with the cup motion. Thus, the magnitude of the output is directly related to the strength of the formed clot. As the clot retracts or lyses, these bonds are broken and the transfer of cup motion is diminished. The rotation movement of the pin 28 is converted by a mechanical-electrical transducer 32 to an electrical signal, which can be monitored by the testing portion 18.

Figure 4:
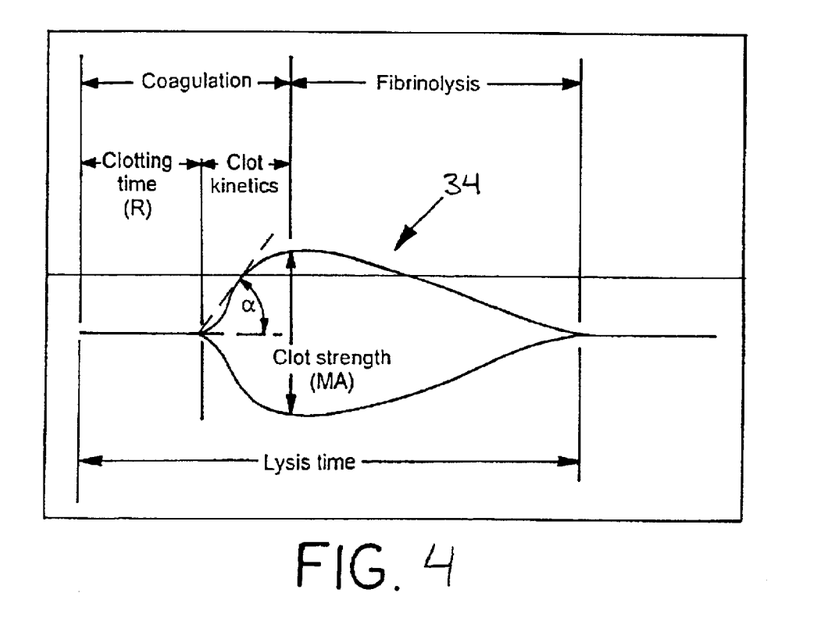
FIG. 4 is a graphic representation of exemplary whole-blood analysis parameters.

The testing portion 18 is operable on the electrical signal to create a hemostasis profile 34 illustrated in FIG. 4, corresponding to the measured clotting process. Additionally, the analysis portion may include a visual display or be coupled to a printer to provide a visual representation of the hemostasis profile. Such a configuration of the computer is well within the skills of one having ordinary skill in the art. The resulting hemostasis profile 34 is a measure of the time it takes for the first fibrin strand to be formed, the kinetics of clot formation, the strength of the clot (in shear elasticity units of $dyn/cm^2$) and dissolution of clot. Table I, below, provides definitions for several of these measured parameters.

TABLE I

| | |
|---|---|
| R | R time is the period of time of latency from the time that the blood was placed in the TEG ® haemostasis analyzer until the initial fibrin formation. |
| α | α measures the rapidity of fibrin build-up and cross-linking (clot strengthening) |
| MA | MA, or Maximum Amplitude, is a direct function of the maximum dynamic properties of fibrin and platelet bonding via GPIIb/IIIa and represents the ultimate strength of the fibrin clot. |
| LY30 | LY30 measures the rate of amplitude reduction 30 minutes after MA and represents lysis. |

Clinically, these measurements provide a vehicle for monitoring anti-coagulation therapy (e.g. heparin or warfarin), thrombolytic therapy (e.g. tissue plasminogen activator (tPA), streptokinase, urokinase), effect of antifibrinolytics (e.g. ε-amino-caproic acid (Amicar), trasylol (aprotinin), tranexamic acid), effect of anti-platelet agents (e.g. abciximab (ReoPro), eptifibatide (Integrilin), tirofiban (Aggrastat), blood component transfusion therapy, thrombotic risk assessment in cancer and infection, high risk surgery and other conditions which could possibly lead to excessive clotting (hypercoagulable conditions) or excessive bleeding (hypocoagulable conditions).

Quantitatively, the blood hemostasis analyzer 12 plots the strength of the clot against time, where the onset of clot formation, the reaction time (R), is noted (see profile 34 illustrated in FIG. 4). This plot also indicates the maximum clot strength (or rigidity), MA, of a blood sample. MA is an overall estimate of platelet-fibrin GPIIb/IIIa bonding, which is used, for example, to guide post-operative blood platelet or fibrinogen replacement therapy. Between platelets and fibrin alone, an abnormally low MA implies that there is an abnormality in blood platelets (i.e., a quantitative or functional defect) and/or an abnormality in fibrinogen content in the blood. However, by keeping fibrinogen level and platelet number constant, any change in MA would reflect changes in platelet function. For example, testing the same blood sample two ways, one with an anti-platelet agent and one without, the difference between the two MAs reflects the effect of the anti-platelet agent on platelet function.

Figure 7A:
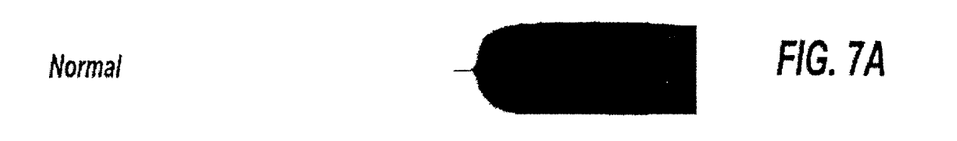
FIGS. 7A–7G are graphic representations of whole-blood analysis parameters for normal hemostasis and various coagulopathy.
Figure 7B:
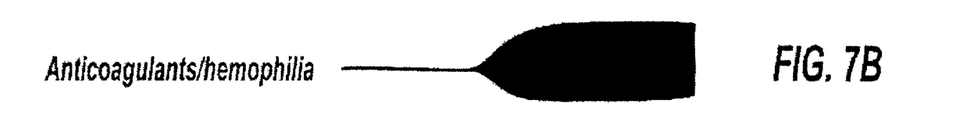
Figure 7C:
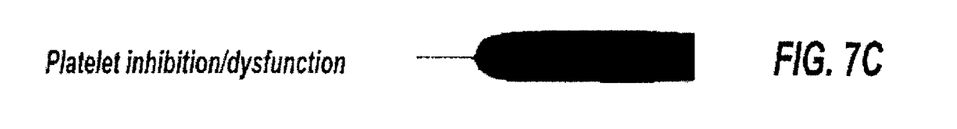
Figure 7D:
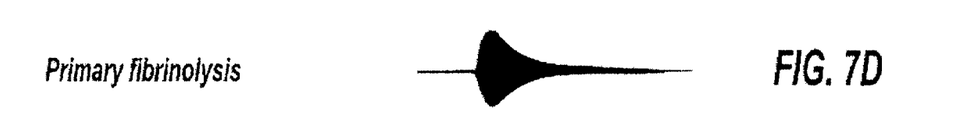
Figure 7E:
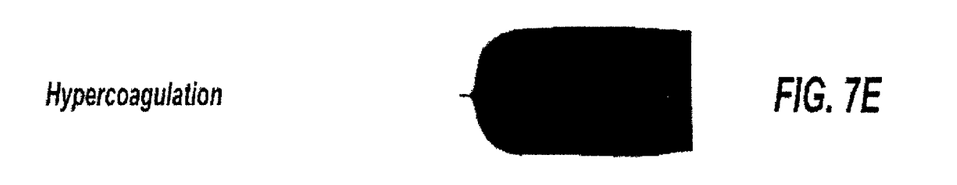
Figure 7F:
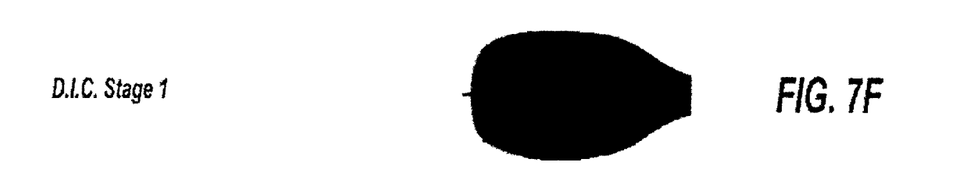
Figure 7G:
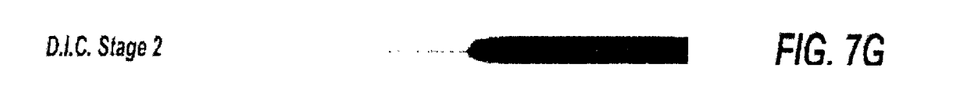

As is appreciated, the hemostasis profile itself is an indication of normal hemostasis, coagulopathy and/or residual anticoagulation therapy. FIGS. 7A–7G illustrate hemostasis profiles illustrating a number of conditions of patient hemostasis. More particularly, FIG. 7A illustrates normal hemostasis. FIG. 7B illustrates hemostasis for a patient suffering from hemophilia or undergoing anticoagulation therapy. FIG. 7C illustrates hemostasis for a patient suffering from poor platelet performance or receiving platelet inhibitor therapy. FIG. 7D illustrates hemostasis for a patient suffering primary fibrinolysis. FIG. 7E illustrates hemostasis for a patient suffering hypercoagulation. FIG. 7F illustrates disseminated intravascular coagulation (D.I.C.) stage 1 hemostasis, and FIG. 7G illustrates D.I.C. stage 2 hemostasis.

Referring again to FIG. 1, system 10 operates to assist the physician or other care giver in diagnosing patient hemostasis. A patient blood sample is deposited within the hemostasis analyzer 12, and the hemostasis analyzer 12 operates to determine a hemostasis parameter, or as explained above, several hemostasis parameters such as a time for initial fibrin formation time R, a fibrin build-up rapidity factor $\alpha$, a clot strength maximum amplitude MA and a rate of amplitude reduction LY30. The parameter(s) is then communicated by the hemostasis analyzer 12 to the analysis tool 14 via the communication network.

As described, the analysis tool 14 may be a personal computer coupled to the network that includes a processor, memory and a control program stored within the memory for operating the processor. The control program includes an algorithm to analyze the parameter(s) to produce a diagnostic result, i.e., an assessment of patient hemostasis. The diagnostic result is then communicated back to the hemostasis analyzer 12/clinician via the network 16. This arrangement offers a number of advantages.

When the algorithm or algorithms used by the analysis tool 14 are updated, which happens periodically as new information relating to hemostasis is developed, it is unnecessary to upgrade the software within the hemostasis analyzer 12. Additionally, the analysis tool 14 may include a database in which is stored data related to particular patients. This data may be directly entered into the analysis tool 14, or it may be provided to the analysis tool by the clinical care facility by electronic data transfer. The data may contain, in addition to information identifying the patient, information relating to the patient's condition, past and current medications, past and current treatment protocols, demographics data, genetic information, and the like. The algorithm may therefore be designed to account for the patient information when generating the diagnostic result.

In addition to the diagnostic result providing an indication of patient hemostasis, the result may further include treatment recommendations. For example, taking into account the patient information, the result may include a recommendation to administer a particular dosage of drug or blood products. The results, and any recommendations, are necessarily based upon a diagnosis/treatment/rule set that is in accordance with the published research and analysis of experts in hematology and pharmaceutical manufacturers.

Any complicated surgical procedure, spontaneous bleeding or clotting, hemostasis dysfunction, or accidental or inflicted injury leaves the patient vulnerable to serious, yet avoidable complications such as acute myocardial infarct, stroke and deviant thrombosis, or hemorrhage. The system and method according to the teachings of the present invention permit a software-assisted diagnostic tool that is available at a moment's notice and lets medical staffers anywhere in the world tap into the collective brain of experts in the field continuously.

In use, experts in the field of hemostasis provide information, for example hemostasis models, that are stored in the database 15 of the analysis tool 14 (see FIG. 2). The analysis tool 14 may include an application interface facilitating entry of model criteria in a standardized format. The model defines criteria for diagnosis and treatment recommendations based on one or more patient measured or observed parameters. The analysis tool control program, in conjunction with the models, evaluates patient results against one or more selected models stored in the database 15 and generates an "approximate measure" score to indicate the closeness or goodness of fit between the patient parameter values and the model values. In addition to the parameter(s) generated by the hemostasis tool 12, the model/control program may factor in other hemostasis tests, demographic information, blood chemistry information, and other patient related information, and suggest a diagnosis and a recommended treatment. The analysis tool 14, via the user interface 13, allows the user to select a model from the various models stored in the database 15, or the patient data may be evaluated against several models to find a "best fit." In addition, or as an alternative, the analysis tool 14 may operate in a "pattern matching" mode, where new patient hemostasis parameters are evaluated with respect to patient related data retained within the database 17 on a statistical basis.

The analysis tool 14 may also be adapted to test models submitted by hematologists and experts in hematology. As mentioned above, the analysis tool 14 may retain patient related data on a statistical basis in the database 17. A model submitted to the analysis tool 14, which submission may be made via the coupled electronic network, can be evaluated against the patient statistical data, including known hemostasis parameters, diagnoses, treatments and results, to validate the model.

While described in terms of a system and method wherein the hemostasis analyzer is directly coupled to the analysis tool 14, other forms of access are contemplated by the invention. For example, a medical professional may access the analysis tool 14 directly via the network 16 using any computer coupled to the network 16 and a suitable interface, such as a web page (which may operate in both online and offline modes) designed to permit access to the analysis tool 14. In such an application, the medical professional may provide the patient information, real or hypothetical, and receive the result generated by the analysis tool 14. Thus, a surgeon may obtain advice during a procedure without ever leaving the operating room.

Figure 8:
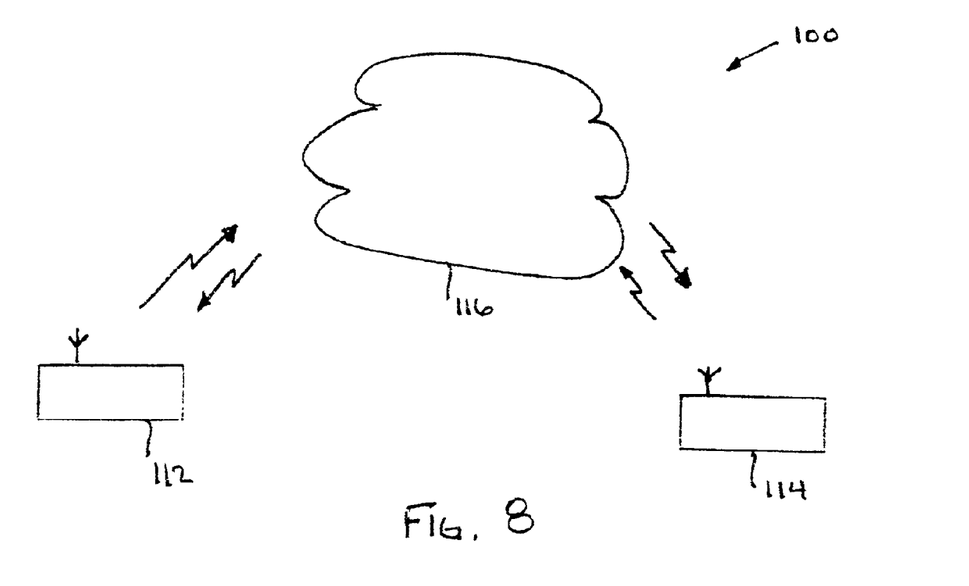
FIG. 8 is a block diagram of a system in accordance with an alternative preferred embodiment of the invention.

The link between the hemostasis analyzer 12, the analysis tool 14 and the network 16 need not be by wired connection, and may be by wireless connection. FIG. 8 illustrates a system 100 including a hemostasis analyzer 112 and an analysis tool 114, each of which is coupled wirelessly to a network 116. The wireless interconnection is not particular to the present invention and may be made by any suitable standard for wireless data including radio-frequency based wireless interconnection and infrared wireless connections. The system 100 otherwise functions as the system 10 to provide a result from parameter data generated by the hemostasis analyzer 112.

Figure 9:
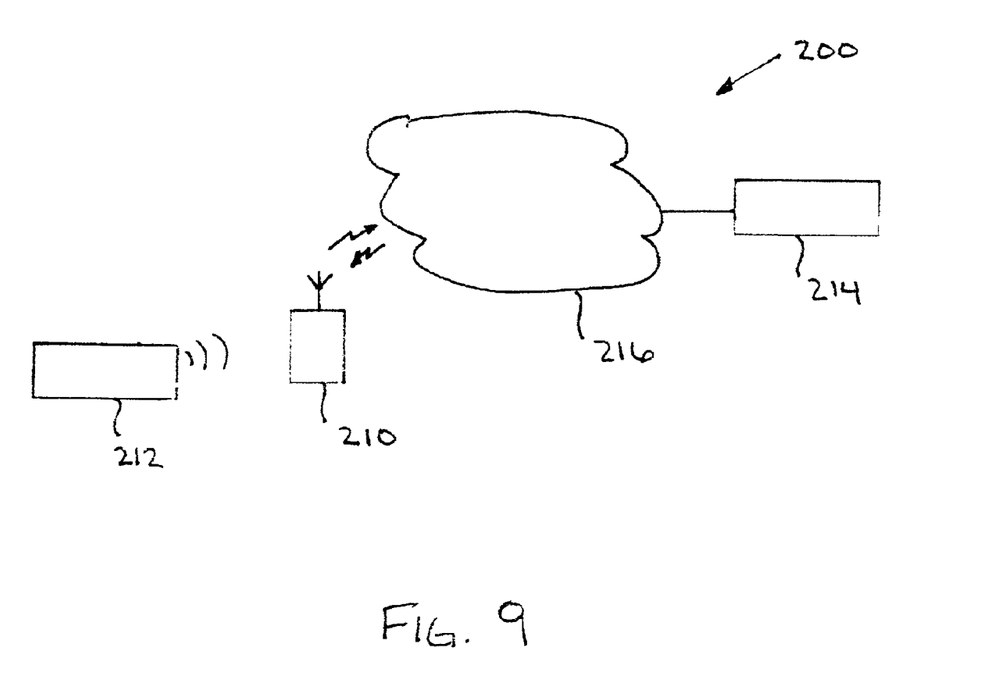
FIG. 9 is a block diagram of a system in accordance with an alternative preferred embodiment of the invention.

FIG. 9 illustrates a system 200 including a hemostasis analyzer 212, an analysis tool 214, and network 216 and an interface tool 210. The analysis tool 214 may be coupled to the network 216 in any suitable manner and a wired connection is illustrated. The interface tool 210, which may be a personal digital assistant (PDA), web enabled cellular telephone, or similar device is coupled to the network 216 by a wireless connection. The hemostasis analyzer 212 communicates with the interface tool 210 using wireless techniques, such as infrared data communication or radio frequency data communication such as Bluetooth radio frequency communication technique. In system 200, the hemostasis parameter(s) may be communicated by the hemostasis analyzer 212 to the interface tool 210. The interface tool 210 may communicate the hemostasis parameter(s) to the analysis tool 214 via the network 216. Alternatively, the interface tool 210, which may include a processor and memory, may download the algorithm and necessary data from the analysis tool 214 via the network for generating a result locally. The interface tool 210 may further be interface with the medical enterprise information management system to acquire patient related information to use in connection with the algorithm and the hemostasis parameter(s) for generating the result.

FIG. 8 and FIG. 9 demonstrate the substantial flexibility of systems and methods designed to operate in accordance with the invention. While several possible alternative interconnection techniques have been illustrated, it will be appreciated that many others are possible. It will be generally appreciated that the invention has been described in terms of several preferred embodiments, which are intended to illustrate the many features and advantage of the invention, but which are not limiting thereof.

Still other modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

We claim:

1. A system for diagnosing hemostasis utilizing a communication network, the system comprising:
    a blood hemostasis analyzer for testing a blood sample and providing at least one parameter indicative of hemostasis, the blood hemostasis analyzer including an interface for communicatively coupling the blood hemostasis analyzer to the communication network;
    an analysis tool communicatively coupled to the communication network, the analysis tool including an algorithm operable on the at least one parameter provide a result; and
    wherein the blood hemostasis analyzer communicates the at least one parameter to the analysis tool via the communication network and the analysis tool generates the result based upon the algorithm and the at least one parameter.

2. The system of claim 1, wherein the at least one parameter comprises one of the parameters selected from the group consisting of a fibrin formation time, a fibrin build-up rapidity factor, a clot strength maximum amplitude and a rate of amplitude reduction.

3. The system of claim 1, wherein the result comprises an indication of patient hemostasis.

4. The system of claim 1, wherein the result comprises a treatment recommendation.

5. The system of claim 1, wherein either of the hemostasis analyzer and the analysis tool are coupled to the communication network wirelessly.

6. The system of claim 1, wherein the analysis tool includes a database of patient information.

7. The system of claim 6, wherein the analysis tool generates the result based upon the algorithm, the parameter and the patient information.

8. The system of claim 1, wherein the algorithm includes signature analysis.

9. A method for diagnosing hemostasis utilizing a communication network, the method comprising the steps of:
    determining a hemostasis parameter from a blood sample;
    communicating using the communication network the hemostasis parameter to an analysis tool including an algorithm; and
    determining a result from the hemostasis parameter using the algorithm.

10. The method of claim 9,
    wherein the step of communicating comprises the step of coupling a hemostasis analyzer to the communication network.

11. The method of claim 9, wherein the step of determining a result comprises providing a treatment recommendation.

12. The method of claim 9 further comprising the step of providing patient related information and the step of determining a result comprises determining the result from the hemostasis parameter and the patient information using the algorithm.

13. The method of claim 9, wherein the step of communicating comprises communicating the hemostasis parameter wirelessly.

14. The method of claim 9, wherein the step of determining a result comprises conducting a signature analysis.

15. A system for diagnosing hemostasis utilizing a communication network comprising:
    a hemostasis analyzer that provides a hemostasis parameter;
    an analysis tool coupled to the communication network, the analysis tool including a processor, a memory and an algorithm retained within the memory, the algorithm operable on the hemostasis parameter for providing a hemostasis indication;
    an interface tool, the interface tool coupled between the hemostasis analyzer and the communication network; and
    wherein the interface tool is in communication with the analysis tool via the communication network for permitting operation by the algorithm on the hemostasis parameter to provide the hemostasis indication.

16. The system of claim 15, wherein the interface tool includes a processor and a memory and the algorithm is downloadable from the analysis tool to the interface tool.

17. The system of claim 15, wherein the hemostasis analyzer is at least one of wired and wirelessly coupled to the interface tool.

18. The system of claim 15, wherein the interface tool is wirelessly coupled to the communication network.

19. The system of claim 15, wherein the interface tool is wirelessly coupled to the hemostasis analyzer.

20. The system of claim 15, wherein the interface tool comprises one of a personal computer, a personal digital assistant and a web enabled wireless communication device.

* * * * *

UNITED STATES PATENT AND TRADEMARK OFFICE
CERTIFICATE OF CORRECTION

PATENT NO. : 6,797,519 B2  Page 1 of 1
APPLICATION NO. : 09/974044
DATED : September 28, 2004
INVENTOR(S) : Eli Cohen et al.

It is certified that error appears in the above-identified patent and that said Letters Patent is hereby corrected as shown below:

In Claim 1, column 9, line 46, please delete "parameter provide" and insert -- parameter to provide --.

Signed and Sealed this

Eighth Day of January, 2008

JON W. DUDAS
*Director of the United States Patent and Trademark Office*